United States Patent [19]

Amschler et al.

[11] Patent Number: 5,236,918
[45] Date of Patent: Aug. 17, 1993

[54] 6-ARYL-3-CYANAMINOPYRIDAZINES, THEIR PREPARATION AND USE AND MEDICAMENTS CONTAINING THEM

[75] Inventors: Hermann Amschler, Radolfzell; Wolf-Rüdiger Ulrich, Konstanz, both of Fed. Rep. of Germany

[73] Assignee: BYK Gulden Lomberg Chemische Fabrik GmbH, Konstanz, Fed. Rep. of Germany

[21] Appl. No.: 768,754

[22] PCT Filed: Apr. 11, 1990

[86] PCT No.: PCT/EP90/00578
§ 371 Date: Dec. 13, 1991
§ 102(e) Date: Dec. 13, 1991

[87] PCT Pub. No.: WO90/12789
PCT Pub. Date: Nov. 1, 1990

[30] Foreign Application Priority Data

Apr. 17, 1989 [CH] Switzerland ............. 01424/89

[51] Int. Cl.⁵ .............. A61K 31/50; C07D 237/20
[52] U.S. Cl. .............. 514/247; 544/224; 544/239
[58] Field of Search .............. 544/224; 514/247

[56] References Cited

U.S. PATENT DOCUMENTS

| | | | |
|---|---|---|---|
| 4,235,928 | 11/1980 | Eicken et al. | 546/323 |
| 4,665,074 | 5/1987 | Amschler | 544/239 |
| 4,707,481 | 11/1987 | Amschler et al. | 544/239 |
| 4,711,959 | 12/1987 | Kluth et al. | 544/321 |

OTHER PUBLICATIONS

Chapleo et al., *J. Med. Chem.* 25, p. 821 (1982).
Stanovnik et al., *J. Heterocyclic. Chem.* 19, p. 577 (1982).

*Primary Examiner*—Emily Bernhardt
*Attorney, Agent, or Firm*—Jacobson, Price, Holman & Stern

[57] ABSTRACT

6-Aryl-3-cyanaminopyridazines and their salts with bases, as well as pharmaceutical compositions containing them, have anti-inflammatory and broncholytic activity, low toxicity and the absence of substantial side effects.

7 Claims, No Drawings

6-ARYL-3-CYANAMINOPYRIDAZINES, THEIR PREPARATION AND USE AND MEDICAMENTS CONTAINING THEM

TECHNICAL FIELD

The invention relates to 6-aryl-3-cyanaminopyridazines, their preparation and use and medicaments containing them.

PRIOR ART

6-Aryl-3-cyanoaminopyridazines are not known.

DESCRIPTION OF THE INVENTION

It has been found that certain 6-aryl-3-cyanaminopyridazines have advantageous pharmacological actions.

The invention relates to 6-aryl-3-cyanaminopyridazines of the general formula I

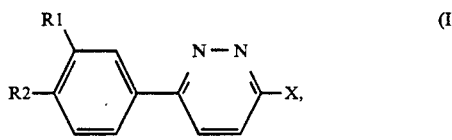

wherein one of the substituents R1 and R2 denotes methoxy, difluoromethoxy or ethoxy and the other denotes C1–C5-alkoxy, C4–C7-cycloalkoxy, C3–C7-cycloalkylmethoxy, C3–C5-alkenyloxy or C1–C4-polyfluoroalkoxy, and X denotes cyanamino, and their salts with bases.

C1–C5-Alkoxy is straight-chained or branched. Examples of C1–C5-alkoxy radicals which may be mentioned are the methoxy, ethoxy, n-propoxy, isopropoxy, n-butoxy, isobutoxy, sec.-butoxy, tert-butoxy, n-pentyloxy, isopentyloxy and the 2,2-dimethylpropoxy radical. C3–C4-Alkoxy is preferred.

C4–C7-Cycloalkoxy represents, for example, cyclobutyloxy, cyclopentyloxy, cyclohexyloxy or cycloheptyloxy, cyclopentyloxy being preferred.

C3–C7-Cycloalkylmethoxy represents, for example, cyclopropylmethoxy, cyclobutylmethoxy, cyclopentylmethoxy, cyclohexylmethoxy or cycloheptylmethoxy, cyclopropylmethoxy and cyclobutylmethoxy being preferred.

C3–C5-Alkenyloxy is straight-chain or branched. The double bond of alkenyloxy does not originate from the carbon atom to which the oxygen atom is bonded. Examples of C3-C5-alkenyloxy radicals which may be mentioned are the buten-2-yloxy, the allyloxy and the methallyloxy radical.

C1–C5-Alkoxy is preferable to C3–C5-alkenyloxy.

C1–C4-Polyfluoroalkoxy is understood as meaning straight-chain or branched C1–C4-alkoxy in which at least 2 hydrogen atoms are replaced by fluorine. Straight-chain C1–C3-alkoxy in which at least 2 hydrogen atoms are replaced by fluorine is preferred. Preferred C1–C4-polyfluoroalkoxy groups are trifluoromethoxy, 1,1,2,2-tetrafluoroethoxy and, in particular, difluoromethoxy and 2,2,2-trifluoroethoxy.

By cyanamino there is understood the —NHCN group.

Possible salts are salts with inorganic and organic bases. The pharmacologically tolerated salts of the inorganic and organic bases usually used in galenics may be mentioned in particular. Salts which are not pharmacologically tolerated and may initially be obtained as process products, for example, in the preparation of the compounds according to the invention on an industrial scale are converted into pharmacologically tolerated salts by processes known to the expert. Examples of such suitable salts are water-soluble and water-insoluble salts with bases, the cations of the alkali metals or alkaline earth metals being used above all as the cations for the salt formation; however, it is also possible to use the corresponding cations of organic nitrogen bases, such as amines or amino-alkanols, amino-sugars etc. Salts which may be mentioned as examples are those of sodium, magnesium, calcium, dimethylamine, diethylamine, ethanolamine, diethanolamine, triethanolamine, glucamine, N-methylglucamine (meglumine), glucosamine and N-methylglucosamine.

One embodiment (embodiment a) of the invention comprises 6-aryl-3-cyanaminopyridazines of the abovementioned general formula I, wherein
  R1 denotes methoxy, difluoromethoxy or ethoxy,
  R2 denotes C1–C4-alkoxy, C4–C6-cycloalkoxy, C3–C6-cycloalkylmethoxy, C3–C4-alkenyloxy or C1–C2-polyfluoroalkoxy and
  X denotes cyanoamino,
and their salts with bases.

A further embodiment (embodiment b) of the invention comprises 6-aryl-3-cyanaminopyridazines of the abovementioned general formula I, wherein
  R1 denotes C2–C4-alkoxy, C4–C6-cycloalkoxy, C3–C6-cycloalkylmethoxy, C3–C4-alkenyloxy or C1–C2-polyfluoroalkoxy,
  R2 denotes methoxy, difluoromethoxy or ethoxy and
  X denotes cyanoamino,
and their salts with bases.

Preferred compounds according to the invention are those of the formula I wherein one of the substituents R1 and R2 denotes methoxy, difluoromethoxy or ethoxy and the other denotes C1–C4-alkoxy, C4–C6-cycloalkoxy, C3–C6-cycloalkylmethoxy or C1–C2-polyfluoroalkoxy, and X denotes cyanoamino, and their salts with bases.

Preferred representatives of embodiment a are those in which R2 denotes C1–C4-alkoxy, C3–C6-cycloalkylmethoxy or C1–C2-polyfluoroalkoxy.

Preferred representatives of embodiment b are those in which R1 denotes C2–C4-alkoxy, C4–C6-cycloalkoxy, C3–C6-cycloalkylmethoxy or C1–C2-polyfluoroalkoxy.

Embodiment b is preferable to embodiment a.

Particularly preferred compounds according to the invention are those of the formula I wherein R1 denotes C2–C4-alkoxy, cyclopentyloxy, cyclopropylmethoxy, cyclobutylmethoxy, difluoromethoxy or 2,2,2-trifluoroethoxy, R2 denotes methoxy, ethoxy or difluoromethoxy and X denotes cyanoamino, and their pharmacologically tolerated salts with bases.

The 6-aryl-3-cyanaminopyridazines according to the invention can exist as tautomeric forms. The proton of the 3-cyanamino group is capable of migrating between this group and the nitrogen in the 2-position of the pyridazine ring. According to the invention, where only one tautomer is mentioned or shown, the other tautomer is also to be understood in each case.

The invention furthermore relates to the use of the compounds according to the invention in the treatment or prophylaxis of illnesses based on a disease of the bronchi.

The invention furthermore relates to the use of the compounds according to the invention and their pharmacologically tolerated salts for the preparation of medicaments for the treatment and/or prophylaxis of diseases of the bronchi.

The invention moreover relates to a process for the preparation of the 3-cyanamino-6-arylpyridazines of the general formula I, wherein R1, R2 and X have the abovementioned meanings, and their salts with bases, which is characterized in that a compound of the general formula I wherein R1 and R2 have the abovementioned meaning and X denotes a leaving group which can be displaced nucleophilically is reacted with an alkali metal cyanamide, preferably sodium cyanamide, in the presence of a phase transfer catalyst in an anhydrous, inert solvent.

By a leaving group which can be displaced nucleophilically there is understood, in particular, a halogen atom, chlorine and bromine being particularly suitable.

The technique of phase transfer catalysis is known to the expert (see e.g. Jozef Dockx, Synthesis 1973, 441-456). Possible phase transfer catalysts are those customary for nucleophilic displacements, in particular for halogen exchange. Suitable catalysts are e.g. crown ethers, quaternary phosphonium salts and, in particular, quaternary ammonium salts, such as e.g. tetrabutylammonium chloride.

The starting compounds are reacted, for example, with at least 2 mol alkali metal cyanamide in a hydrocarbon, such as e.g. toluene or xylene, or in an ether, such as e.g. dioxane, or a ketone, such as e.g. 2-methyl-4-pentanone (isobutyl methyl ketone), or an N,N-disubstituted acid amide, such as e.g. dimethylformamide or N-methylpyrrolidone, under anhydrous conditions in the presence of 0.1 to 2 mol of the phase transfer catalyst at temperature of 50° to 200° C., in particular 80° to 150° C., preferably at the boiling point of the solvent.

The 6-aryl-3-cyanaminopyridazines are converted into the salts by methods which are known to the expert. The alkaline reaction partner used is that inorganic or organic base of which the salt is desired. The salts are obtained, for example, by reacting the 6-aryl-3-cyanaminopyridazines with the stoichiometric equivalent of the corresponding base, e.g. sodium hydroxide or sodium methanolate, or readily soluble salts are converted into sparingly soluble salts by double decomposition.

To prepare the compounds of embodiments a and b, corresponding starting compounds of the general formula I wherein R1 and R2 have the meaning given above in each case and X denotes a leaving group which can be displaced nucleophilically are employed.

The starting compounds of the general formula I wherein X denotes a leaving group which can be displaced nucleophilically are new and the invention also relates to these compounds. They can be prepared by known processes, for example by reaction of 6-aryl-3[2H]pyridazinones of the formula II

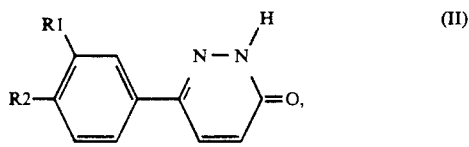

wherein R1 and R2 have the meaning given above in each case, with a phosphorus oxytrihalide, such as phosphorus oxytrichloride, in excess in an inert solvent, such as toluene or xylene, or without a solvent.

The starting compounds of the formula II are known, or they can be prepared by known processes, such as are described e.g. in European Patent 163,965.

The following examples serve to illustrate the invention in more detail. m.p. denotes melting point, b.p. denotes boiling point.

EXAMPLES

End products

1.

3-Cyanamino-6-(3-methoxy-4-n-propoxyphenyl)pyridazine 1.8 g 3-chloro-6-(3-methoxy-4-n-propoxyphenyl)-pyridazine, 0.8 g sodium cyanamide and 3.6 g tetrabutylammonium chloride are boiled under reflux in 30 ml dry toluene for 5 hours. The reaction mixture is then evaporated in vacuo and the residue is boiled up briefly with 200 ml 2 N sodium hydrogen sulphate solution, while stirring thoroughly, the reaction product precipitating as a fine crystalline precipitate. The precipitate is filtered off with suction, washed with water and dried in vacuo. For purification, it is boiled up briefly with 50 ml isopropanol, filtered off with suction and dried in vacuo. This gives 1.5 g (83.3%) of the title compound of m.p. 187° C.

2.

3-Cyanamino-6-(3-ethoxy-4-methoxyphenyl)pyridazine 2.7 g 3-chloro-6-(3-ethoxy-4-methoxyphenyl)pyridazine, 1.3 g sodium cyanamide and 0.5 g benzyltriethylammonium chloride are heated at 150° C. in 30 ml N-methylpyrrolidone for 3 hours. After cooling the reaction solution is diluted with 200 ml 1N sulphuric acid and extracted 3 times with 50 ml chloroform each time. The combined extracts are dried over sodium sulphate and evaporated and the residue is boiled up in isopropanol. The crystalline product is filtered off with suction, washed with isopropanol and dried in vacuo. This gives 2.6 g (96.3%) of the title compound of m.p. 206° C.

3.

3-Cyanamino-6-[4-(2-methylpropoxy)-3-methoxyphenyl]pyridazine 3 g 3-bromo-6[4-(2-methylpropoxy)-3-methoxyphenyl]pyridazine, 1.3 g sodium cyanamide and 0.5 g 18-crown-6 are boiled under reflux in 30 ml 2-methyl-4-pentanone for 5 hours. The reaction solution is then evaporated in vacuo and the residue is boiled up briefly with 200 ml 2N sodium hydrogen sulphate solution, while stirring thoroughly, the reaction product precipitating as a fine crystalline precipitate. The precipitate is filtered off with suction and boiled up again with isopropanol, the mixture is cooled and the product is filtered off with suction and, after washing with isopropanol and petroleum spirit (b.p. 50°-70° C.), dried in vacuo. This gives 2.5 g (80.6%) of the title compound of m.p. 191° C.

4.

3-Cyanamino-6-[4-(3-methylbut-1-oxy)-3-methoxyphenyl]pyridazine 6 g 3-chloro-6-[4-(3-methylbut-1-oxy)-3-methoxyphenyl]pyridazine, 2.5 g sodium cyanamide and 10.3 g tetrabutylammonium chloride are boiled under reflux in 80 ml dioxane for 6 hours. After cooling, the reaction mixture is diluted with 200 ml 2N sulphuric acid, the reaction product separating out in crystalline form. The precipitate is filtered off with suction, washed neutral with water, suspended in acetone again, filtered off with suction and dried in vacuo. This gives 3.6 g (59%) of the title compound of m.p. 223° C.

The following compounds are obtained analogously, using corresponding 3-chloro-6-arylpyridazines:

3-Cyanamino-6-[4-methoxy-3-(1-methylethoxy)-phenyl]pyridazine, m.p. 210° C. (89%),
3-Cyanamino-6-[4-methoxy-3-(2-methylpropoxy)-phenyl]pyridazine, m.p. 213° C. (70%),
3-Cyanamino-6-[3-methoxy-4-(1-methylethoxy)-phenyl]pyridazine, m.p. 223° C. (59%),
3-Cyanamino-6-(4-ethoxy-3-methoxyphenyl)pyridazine, m.p. 221° C. (56%),
3-Cyanamino-6-(4-difluoromethoxy-3-methoxyphenyl)pyridazine, m.p. 209° C. (83%),
3-Cyanamino-6-(3-difluoromethoxy-4-methoxyphenyl)pyridazine, m.p. 226' C. (79%),
3-Cyanamino-6-(3,4-dimethoxyphenyl)pyridazine, m.p. 246° C. (78%),
3-Cyanamino-6-(3-cyclopentyloxy-4-methoxyphenyl)pyridazine, m.p. 231° C. (92%),
3-Cyanamino-6-(4-difluoromethoxy-3-ethoxyphenyl)pyridazine, m.p. 188° C. (74%),
3-Cyanamino-6-[4-ethoxy-3-(2-methylpropoxy)phenyl]pyridazoine, m.p. 203° C. (82%),
3-Cyanamino-6-(3-difluoromethoxy-4-ethoxyphenyl)pyridazine, m.p. 212° C. (74%),
3-Cyanamino-6-(3-cyclobutylmethoxy-4-methoxyphenyl)pyridazine, m.p. 202° C. (95%),
3-Cyanamino-6-[4-difluoromethoxy-3-(1-methylethoxy)phenyl]pyridazine, m.p. 188° C. (94%),
3-Cyanamino-6-(3-cyclopentyloxy-4-difluoromethoxyphenyl)pyridazine, m.p. 215° C. (90%), m.p. of the meglumine salt: 124° C.,
3-Cyanamino-6-(3-cyclopropylmethoxy-4-difluoromethoxyphenyl)pyridazine, m.p. 189° C. (96%),
3-Cyanamino-6-[4-difluoromethoxy-3-(2-methylpropoxy)phenyl]pyridazine, m.p. 203°–204° C. (45%),
3-Cyanamino-6-[4-difluoromethoxy-3-(2,2,2-trifluoroethoxy)phenyl]pyridazine, m.p. 200° C. (98%), m.p. of the sodium salt: 290° C.,
3-Cyanamino-6-(4-cyclopropylmethoxy-3-difluoromethoxyphenyl)pyridazine, m.p. 194° C. (95%).

STARTING COMPOUNDS

3-Chloro-6-(3-methoxy-4-n-propoxyphenyl)pyridazine 18.0 g 6-(3-methoxy-4-n-propoxyphenyl)-3[2H]pyridazinone are suspended in 63.6 g phosphorus oxytrichloride. The mixture is stirred at 100° C. until a clear solution has formed and the evolution of HCl stops. The solution is cooled to about 50° C. and poured onto 1 kg of ice, while stirring constantly, whereupon a crystalline precipitate forms immediately, this being filtered off with suction and washed free from acid with water, dilute sodium bicarbonate solution and again with water. Drying in vacuo gives 19.1 g (98.8%) of the title compound of m.p. 129° C., and of m.p. 132° C. after crystallization from cyclohexane.

The following 3-chloro-6-arylpyridazines are obtained analogously using corresponding 6-aryl-3[2H]pyridazinones:

3-Chloro-6-[4-methoxy-3-(1-methylethoxy)phenyl]pyridazine, m.p. 148° C. (92%),
3-Chloro-6-(3-ethoxy-4-methoxyphenyl)pyridazine, m.p. 141° C. (63%),
3-Chloro-6-[4-methoxy-3-(2-methylpropoxy)phenyl]pyridazine, m.p. 138° C. (97%),
3-Chloro-6-[3-methoxy-4-(2-methylpropoxy)phenyl]pyridazine, m.p. 116° C. (95%),
3-Chloro-6-(3-difluoromethoxy-4-methoxyphenyl)pyridazine, m.p. 156° C. (98%),
3-Chloro-6-(4-difluoromethoxy-3-methoxyphenyl)pyridazine, m.p. 155° C. (97%),
3-Chloro-6-[3-methoxy-4-(3-methylbutoxy)phenyl]pyridazine, m.p. 98° C. (87%),
3-Chloro-6-[3-methoxy-4-(1-methylethoxy)phenyl]pyridazine, m.p. 115° C. (63%),
3-Chloro-6-(4-ethoxy-3-methoxyphenyl)pyridazine, m.p. 145° C. (94%),
3-Chloro-6-(3,4-dimethoxy-phenyl)pyridazine, m.p. 158° C. (76%),
3-Chloro-6-(3-cyclopentyloxy-4-methoxyphenyl)pyridazine, m.p. 141° C. (80%),
3-Chloro-6-[4-ethoxy-3-(2-methylpropoxy)phenyl]pyridazine, m.p. 155° C. (77%),
3-Chloro-6-(4-difluoromethoxy-3-ethoxyphenyl)pyridazine, m.p. 125° C. (87%),
3-Chloro-6-(3-difluoromethoxy-4-ethoxyphenyl)pyridazine, m.p. 165° C. (94%),
3-Chloro-6-(3-cyclobutylmethoxy-4-methoxyphenyl)pyridazine, m.p. 159° C. (98%),
3-Chloro-6-(3-cyclopentyloxy-4-difluoromethoxyphenyl)pyridazine, m.p. 95.5°–96° C. (68%),
3-Chloro-6-[4-difluoromethoxy-3-(1-methylethoxy)phenyl]pyridazine, m.p. 90° C. (97%),
3-Chloro-6-(3-cyclopropylmethoxy-4-difluoromethoxyphenyl)pyridazine, m.p. 140° C. (35%),
3-Chloro-6-(4-difluoromethoxy-3-(2,2,2-trifluoroethoxy)phenyl]pyridazine, m.p. 109° C. (93%),
3-Chloro-6-(4-cyclopropylmethoxy-3-difluoromethoxyphenyl)pyridazine, m.p. 122.5° C. (12%),
3-Chloro-6-[4-difluoromethoxy-3-(2-methylpropoxy)phenyl]pyridazine, m.p. 121°–122° C. (97%).

COMMERCIAL USEFULNESS

The 6-aryl-3-cyanaminopyridazines according to the invention have valuable pharmacological properties which render them commercially usable. They are distinguished above all by those properties which suggest they are suitable for the therapy of diseases of the respiratory tract of various origins. In particular, inflammatory and allergen-induced bronchial diseases can be treated on the basis of the antiinflammatory and bronocholytic activity of the compounds according to the invention. In addition, the compounds according to the invention are distinguished by a low toxicity, a wide therapeutic range and the absence of substantial side effects.

The broncholytic and antiinflammatory activity of the 6-aryl-3-cyanaminiopyridazines enables them to be used in human and veterinary medicine, in which they are used for the treatment and prophylaxis of illnesses based on diseases of the bronchi. For example, acute and chronic obstructive diseases of the respiratory tract of various origins (bronchitis, allergic bronchitis, bronchial asthma) in humans and animals can be treated.

The invention thus furthermore relates to a process for the treatment of mammals, including humans, suffering from one of the abovementioned diseases. The process is characterized in that a therapeutically active and pharmacologically tolerated amount of one or more of the compounds according to the invention is administered to the sick mammal.

The invention furthermore relates to the compounds according to the invention for use in the treatment and/or prophylaxis of illnesses based on diseases of the bronchi.

The invention similarly relates to the use of the compounds according to the invention for the preparation of medicaments which are employed for the treatment and/or prophylaxis of illnesses based on diseases of the bronchi.

The invention furthermore relates to medicaments for the treatment and/or prophylaxis of illnesses based on diseases of the bronchi, which contain one or more of the compounds according to the invention and/or their pharmacologically tolerated salts.

The medicaments according to the invention are prepared by processes which are known per se, reference being made, for example, to the statements in European Patent No. 163 965 in respect of the formulations, dosages, presentation forms etc.

EXAMPLES OF MEDICAMENT FORMULATIONS

Tablets containing 100 mg 3-cyanamino-6-[4-(2-methylpropoxy)-3-methoxyphenyl]pyridazine 40 kg active compound, 24 kg lactose and 16 kg maize starch are granulated with 4 kg polyvinylpyrrolidone (MW about 25,000) in 5.5 liters water and the granules are forced through a sieve of 1.25 mm mesh width. After drying, 10 kg carboxymethylcellulose, 4 kg talc and 2 kg magnesium stearate are added. The granules are pressed to tablets of 9 mm diameter and 250 mg weight with a hardness of 4 to 5 kg on an eccentric machine.

Capsules containing 15 mg 3-cyanamino-6-[3-(1-methylethoxy)-4-methoxyphenyl]-pyridazine 150 mg active compound, 845 mg microcrystalline cellulose and 5 mg amorphous silicic acid are finely powdered, mixed thoroughly and introduced into size 4 hard gelatine capsules.

Metered aerosol formulation containing 3-cyanamino-6-(3-ethoxy-4-methoxyphenyl)pyridazine 0.540 g Span ®85 and 0.135 g aroma are dissolved in 10.215 g cooled Frigen ®11. 0.270 g micronized active compound is stirred into the solution and the mixture is introduced into 24 ml cans. After crimping, 14.971 g Frigen ®12 are forced in. At a chamber volume of the metering valve of 125 µl, 1.6 mg active compound are released as aerosol per valve stroke.

BIOLOGICAL STUDIES

The compounds investigated are identified by numbers in the tables which follow:
3-Cyanamino-6-(3-methoxy-4-n-propoxyphenyl)pyridazine
3-Cyanamino-6-(3-ethoxy-4-methoxyphenyl)pyridazine
3-Cyanamino-6-[4-methoxy-3-(1-methylethoxy)-phenyl]pyridazine
3-Cyanamino-6-[4-methoxy-3-(2-methylpropoxy)-phenyl]pyridazine
3-Cyanamino-6-[3-methoxy-4-(2-methylpropoxy)-phenyl]pyridazine
3-Cyanamino-6-[3-methoxy-4-(1-methylethoxy)-phenyl]pyridazine
3-Cyanamino-6-(4-ethoxy-3-methoxyphenyl)pyridazine
3-Cyanamino-6-(4-difluoromethoxy-3-methoxyphenyl)-pyridazine
3-Cyanamino-6-(3-difluoromethoxy-4-methoxyphenyl)-pyridazine
3-Cyanamino-6-(3,4-dimethoxyphenyl)pyridazine
3-Cyanamino-6-(3-cyclopentyloxy-4-methoxyphenyl)-pyridazine
3-Cyanamino-6-(4-difluoromethoxy-3-ethoxyphenyl)-pyridazine
3-Cyanamino-6-[4-ethoxy-3-(2-methylpropoxy)phenyl]-pyridazine
3-Cyanamino-6-(3-difluoromethoxy-4-ethoxyphenyl)-pyridazine
3-Cyanamino-6-(3-cyclobutylmethoxy-4-methoxyphenyl)pyridazine
3-Cyanamino-6-[4-difluoromethoxy-3-(1-methylethoxy)phenyl]pyridazine
3-Cyanamino-6-(3-cyclopentyloxy-4-difluoromethoxyphenyl)pyridazine
3-Cyanamino-6-(3-cyclopropylmethoxy-4-difluoromethoxyphenyl)pyridazine
3-Cyanamino-6-[4-difluoromethoxy-3-(2-methylpropoxy)phenyl]pyridazine
3-Cyanamino-6-[4-difluoromethoxy-3-(2,2,2-trifluoroethoxy)phenyl] pyridazine
3-Cyanamino-6-(4-cyclopropylmethoxy-3-difluoromethoxyphenyl)pyridazine The bronchospasmolytic action of the compounds on the tracheal ring chain of the guinea-pig was tested in vitro as follows: Four parallel tracheal ring chains, each consisting of 6 individual rings, of the guinea-pig (female and male, 430–600 g), in an organ bath [5 ml, Krebs-Henseleit solution with addition of phentolamine ($10^{-5}$ mol/l), 37° C., pretension of the organs 2 g, gassing with carbogen] develop a stable, tonic spontaneous contraction after about 20 to 30 minutes. Relaxation can be brought about on these permanently contracted organs under isometric measurement conditions by application of the test substance in a cumulatively semilogarithmically increasing concentration (e.g. $1 \times 10^{-6} + 2 \times 10^{-6} + 7 \times 10^{-6} + 2 \times 10^{-5}$ etc. mol/l), a constant relaxation response being awaited after each individual dose of the test substance before the next higher concentration is applied. A complete dose/effect curve of the test substance is thus obtained over a period of 20 to 30 minutes. The particular relaxation is expressed as the percentage fraction of the maximum relaxation which can be achieved by addition of (−)isoprenaline ($10^{-6}$ mol/l). The concentration of the test substance which causes 50% of the maximum relaxation which can be achieved serves as a measure of the bronchodilatory activity, expressed by the negative logarithm of the $EC_{50}$ mol/l: $-\log[EC_{50}]$.

The values of $-\log[EC_{50}]$ and the quotients of the $EC_{50}$ values for theophylline and the substance investigated are shown in table 1. The values found show that the compounds according to the invention are greatly superior to theophylline in respect of the bronchospasmolytic activity.

TABLE 1

| No. | $-\log[EC_{50}]$ | $[EC_{50}]_{theophylline}/[EC_{50}]_{substance}$ |
|---|---|---|
| 1 | 5.25 | 24.0 |
| 2 | 5.52 | 44.7 |
| 3 | 6.38 | 324 |
| 4 | 6.95 | 1203 |
| 5 | 5.45 | 38.1 |
| 6 | 5.09 | 16.6 |
| 7 | 5.19 | 20.9 |
| 8 | 5.73 | 72.5 |
| 9 | 5.63 | 57.6 |
| 10 | 5.15 | 19.1 |
| 11 | 6.25 | 240 |
| 12 | 5.61 | 55.0 |
| 13 | 6.27 | 251 |
| 14 | 5.69 | 66.1 |
| 15 | 6.04 | 148 |
| 16 | 6.18 | 204 |
| 17 | 6.12 | 178 |
| 18 | 6.25 | 240 |
| 19 | 5.85 | 95.6 |
| 20 | 5.64 | 58.9 |
| 21 | 6.00 | 135 |
| Theophylline | 3.87 | 1 |

The trachea-relaxing action of compounds 3 and 4 was additionally tested by relaxation of the contractions generated by histamine (His), carbachol (CC), prostaglandin (PGF$_{2alpha}$), ovalbumin (OA) and leukotriene (LTC$_4$). As can be seen from the measurement values shown in Table 2, the compounds according to the invention also display a greatly increased relaxation compared with theophylline under the modified conditions.

TABLE 2

| Contraction by | 3 | 4 | Theophylline |
|---|---|---|---|
| His ($10^{-5}$) | 6.15 | 6.64 | 3.76 |
| CC ($10^{-6}$M) | 5.59 | 5.98 | 3.24 |
| PGF$_{Zalpha}$ ($10^{-6}$M) | 6.35 | 6.82 | 3.77 |
| OA ($10^{-5} - 10^{-4}$ mg/ml) | 6.19 | 6.40 | 3.54 |
| LTC$_4$ ($5 \times 10^{-8}$M) | 6.19 | 6.84 | 3.67 |

The bronchospasmolytic action was furthermore determined on the model of "histamine-induced bronchospasm on the anaesthetized guinea-pig":

In this model, pharmacodynamic and toxic effects on internal sensitive receptors, on the respiration and on the cardiovascular system of guinea-pigs are recorded simultaneously [U. Kilian, E. Müller, E. Ch. Dittmann and J. Hamacher, Arzneimittel-Forschung 28 (II) 1699-1708, 1978]. The pneumotachogram of anaesthetized (ethylurethane 1.25 g/kg i.p.) monovagotomized, spontaneously respirating guinea-pigs (male, 350-450 g) was recorded and the maximum flow rate of the respiratory air during expiration (Vmax$_e$) was measured to characterize the bronchospasm induced by histamine (0.09-0.18 mol/kg i.v.).

A histamine spasm before administration of the substance was compared with several histamine spasms after administration of the substance. The test substances were administered intravenously (i.v.) and/or intrajejunally (i.j.).

It was found that the compounds investigated inhibit the histamine-induced bronchospasm on anaesthetized guinea-pigs to an approximately 2-5 times greater degree than theophylline.

TABLE 3

Average percentage bronchospasmolytic action 0-1 h p. appl., measured by the inhibition of the histamine-induced decrease in Vmax$_e$

| No. | Dose μmol/kg | % inihibition after i.v. | % inihibition after i.j. administration |
|---|---|---|---|
| 3 | 20 | 28 | 29 |
|   | 60 | 65 | 65 |
| 4 | 20 | 37 | 39 |
|   | 60 | 87 | 60 |
| 12 | 20 | 50 | — |
| 13 | 20 | 28 | — |
| Theophilline | 20 | 13 | 11 |
|   | 60 | 25 | 37 |
|   | 100 | 34 | 45 |

The bronchospasmolytic action was additionally tested on the model of "Protective action against acetylcholine-induced bronchospasm on the conscious guinea-pig":

The experiments were carried out in accordance with the method of T. Olsson, Acta Allergologica 26, 438-447 (1971). Guinea-pigs (250-350 g) are exposed in a closed Plexiglas cylinder (volume 5 l) to an acetylcholine mist (0.06% in 0.9% sodium chloride solution; ultrasonic mister Heyer Use 77) twice before administration of the substance at an interval of 20 minutes, and 30 minutes after administration of the substance. The time from the start of misting to the onset of clear respiratory exertion (under certain circumstances hypoxic convulsions in the lateral position) is measured and defined as the latency period. A prolonging of the latency period after administration of the substance to at least three times the average latency period before administration of the substance is regarded as a protective action, and the number of protected animals in the group is stated. The test substances are administered orally by means of a stomach tube (dose 100 μmol/kg, volume 1 ml/kg, suspending agent 4% Methocel suspension in 0.9% sodium chloride solution).

In the control experiment (without administration of the substance), the latency period is 2 minutes. The test substance is administered perorally by means of a stomach tube (standard dose 100 μmol, volume 1 ml 4% Methocel suspension in 0.9% sodium chloride solution/kg). After 30 minutes, the animals are exposed to the acetylcholine mist again and the latency periods are measured. Prolonging of the latency period to at least three times the length is regarded as a protective action.

It can be seen from Table 4 that the compounds investigated have a protective action which is comparable or superior to that of theophylline.

TABLE 4

Protective action against acetylcholine-induced bronchospasm on the conscious guinea-pig, determined 30 minutes after oral administration of the substance or placebo. Dose: 100 μmol/kg of the test substance (= verum) or substance-free suspending agent (= placebo).

| No. | Number of animals protected/ number of animals used Verum | placebo |
|---|---|---|
| 3 | 14/20 | 5/20 |
| 4 | 17/20 | 5/20 |
| 12 | 14/20 | 4/20 |
| 13 | 13/20 | 5/20 |
| 16 | 10/20 | 4/20 |
| 18 | 10/20 | 4/20 |
| 20 | 11/20 | 4/20 |
| Theophylline | 6/20 | 2/20 |

The inhibition of phosphodiesterases of classes III (PDE III = high-affinity cAMP-PDE which can be inhibited by cGMP) and IV (PDE IV = high-affinity cAMP-PDE which cannot be inhibited by cGMP, Rolipram-sensitive) is regarded as being particularly conclusive for a bronchospasmolytic and/or antiinflammatory action which may be expected [H. Hidaka et al., Adv. Cycl. Nucl. Res. 13, 145 (1984); Tips 5, 237 (1984); R. Weishaar et al., J. Med. Chem. 28, 537 (1985); S. A. Harrison et al., Molec. Pharmac. 29, 506 (1986); J. Klein-Tebbe et al., Allergologie 12, 12 (1989); C. Schudt et al., Allergologie 12, 12 (1989)].

The PDE inhibition of the compounds according to the invention was therefore determined on a PDE III isolated from human platelets and PDE IV isolated from human neutrophilic polymorphonuclear cells (PMNs) and from the canine trachea. The phosphodiesterases III and IV are isolated by chromatography by the method of Polson et al., Biochem. Pharmacol. 31, 3403–3406 (1982).

The substances are dissolved in DMSO and diluted further. From a series of solutions diluted up to a hundred-fold, 2.1 μl portions are taken and 212 μl reaction mixture are added. The reaction mixture contains Hepes (100 mmol/l), DTE (5 mmol/l), $MgCl_2$ (5 mmol/l), $CaCl_2$ (10 μmol/l), BSA fraction V 0.5 mg/ml, cAMP 0.5 μmol/l, 2,8-$^3$H-cAMP 250,000 cpm/ml (0.3 μCi/ml, s.a. 33.5 μCi/mmol) and SV (snake venom) (25 μg/212 μl test batch).

The reaction is started by addition of 10 μl PDE to the reaction mixture and to the substance batch. The mixtures are then incubated at 37° C. for 20 minutes. The reaction is stopped by heating at 95° C. for 45 seconds. After the samples have cooled, the SV solution is added, the 5-AMP formed being cleaved. After incubation for 30 minutes at 37° C., this reaction is stopped by addition of 1 ml anion exchanger suspension. The cAMP which remains is thereby bonded. The adenosine formed remains in the supernatant after centrifugation and can be measured in an aliquot by the radioactivity contained therein. The $IC_{50}$ values are determined in a Hill plot with linear regression. p The negative logarithms of the $IC_{50}$ values found and the quotients of the $IC_{50}$ value determined for theophylline and the $IC_{50}$ values of the substances according to the invention are shown in Tables 5, 6 and 7. The substances according to the invention inhibit PDE III and PDE IV to a significantly greater degree than theophylline.

TABLE 5

| | Inhibition of PDE III | |
|---|---|---|
| No. | $-\log[IC_{50}]PDE\ III$ | $[IC_{50}]_{theophylline}/[IC_{50}]_{substance}$ |
| 2 | 4.98 | 15.5 |
| 3 | 5.28 | 30.8 |
| 4 | 5.22 | 26.9 |
| 6 | 5.20 | 25.7 |
| 7 | 5.05 | 18.2 |
| 9 | 4.91 | 13.2 |
| 10 | 4.97 | 15.1 |
| Theophylline | 3.79 | 1 |

TABLE 6

| | Inhibition of PDE IV from the canine trachea | |
|---|---|---|
| No. | $-\log[IC_{50}]$PDE IV canine trachea | $[IC_{50}]_{theophylline}/[IC_{50}]_{substance}$ |
| 2 | 5.79 | 95.6 |
| 3 | 5.75 | 82.2 |
| 4 | 6.36 | 355 |

TABLE 6-continued

| | Inhibition of PDE IV from the canine trachea | |
|---|---|---|
| No. | $-\log[IC_{50}]$PDE IV canine trachea | $[IC_{50}]_{theophylline}/[IC_{50}]_{substance}$ |
| 7 | 5.32 | 32.4 |
| 8 | 5.66 | 70.8 |
| 9 | 5.65 | 69.2 |
| 10 | 5.68 | 74.1 |
| 11 | 5.89 | 120 |
| 12 | 5.80 | 97.8 |
| 15 | 5.70 | 77.7 |
| Theophylline | 3.81 | 1 |

TABLE 7

| | Inhibition of PDE IV from human neutrophilic polymorphonuclear cells (PMNs) | |
|---|---|---|
| No. | $-\log[IC_{50}]PDE\ IV$ PNMs | $[IC_{50}]_{theophylline}/[IC_{50}]_{substance}$ |
| 3 | 5.82 | 117 |
| 4 | 6.33 | 357 |
| 11 | 6.22 | 288 |
| 13 | 6.18 | 263 |
| 14 | 5.69 | 85.1 |
| 16 | 6.50 | 550 |
| 17 | 6.47 | 513 |
| 18 | 6.64 | 759 |
| 19 | 6.48 | 525 |
| 20 | 5.93 | 148 |
| Theophylline | 3.76 | 1 |

We claim:

1. A 6-aryl-3-cyanaminopyridazine of the formula I

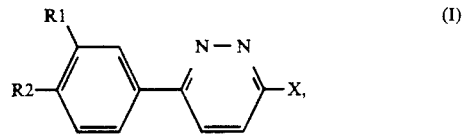

wherein one of the substituents R1 and R2 denotes methoxy, difluoromethoxy or ethoxy and the other denotes C1–C5-alkoxy, C4–C7-cycloalkoxy, C3–C7-cycloalkylmethoxy, C3–C5-alkenyloxy or C1–C4-polyfluoroalkoxy, and X denotes cyanamino, or a salt; with a base.

2. A compound of formula I according to claim 1, wherein

R1 denotes methoxy, difluoromethoxy or ethoxy,
R2 denotes C1–C4-alkoxy, C4–C6-cycloalkoxy, C3–C6-cycloalkylmethoxy, C3–C4-alkenyloxy or C1–C2-polyfluoroalkoxy and
X denotes cyanamino, or a salt, with a base.

3. A compound of formula I according to claim 1, wherein

R1 denotes C2–C4-alkoxy, C4–C6-cycloalkoxy, C3–C6-cycloalkylmethoxy, C3–C4-alkenyloxy or C1–C2-polyfluoroalkoxy,
R2 denotes methoxy, difluoromethoxy or ethoxy and
X denotes cyanamino, or a salt, with a base.

4. A compound of formula I according to claim 1, wherein one of the substituents R1 and R2 denotes methoxy, difluoromethoxy or ethoxy and the other denotes C1–C4-alkoxy, C4–C6-cycloalkoxy, C3–C6-cycloalkylmethoxy or C1–C2-polyfluoroalkoxy, and X denotes cyanamino, or a salt, with a base.

5. A compound of formula I according to claim 1, wherein R1 denotes C2–C4-alkoxy, cyclopentyloxy, cyclopropylmethoxy, cyclobutylmethoxy, difluoromethoxy or 2,2,2-trifluoroethoxy, R2 denotes methoxy, ethoxy or difluoromethoxy and X denotes cyanamino, or a pharmacologically tolerated salt, with a base.

6. A medicament composition useful for treatment and/or prophylaxis of a bronchial disorder and which comprises an effective amount of a compound of claim 1 or of a pharmaceutically-acceptable salt thereof with a base and a pharmacologically-acceptable carrier.

7. Treatment or prophylaxis of a bronchial disorder which comprises administering an effective amount of a pharmacologically-acceptable active ingredient to a mammal afflicted with the bronchial disorder, wherein the active ingredient is a compound of claim 1 or a physiologically-acceptable salt thereof with a base.

* * * * *